(12) United States Patent
Romo et al.

(10) Patent No.: US 8,979,782 B2
(45) Date of Patent: Mar. 17, 2015

(54) HINGE USED FOR THE TREATMENT OF ANTERIOR AND POSTERIOR CRUCIATE LIGAMENT INJURY AND METHOD FOR USING THE SAME

(71) Applicant: Össur hf, Reykjavik (IS)

(72) Inventors: Harry Duane Romo, Aliso Viejo, CA (US); Bjorn Thor Omarsson, Reykjavik (IS); Arni Thor Ingimundarson, Gardabaer (IS)

(73) Assignee: Ossur HF, Reykjavik (IS)

( * ) Notice: Subject to any disclaimer, the term of this patent is extended or adjusted under 35 U.S.C. 154(b) by 274 days.

(21) Appl. No.: 13/707,014

(22) Filed: Dec. 6, 2012

(65) Prior Publication Data

US 2013/0150761 A1 Jun. 13, 2013

Related U.S. Application Data

(60) Provisional application No. 61/567,813, filed on Dec. 7, 2011.

(51) Int. Cl.
*A61F 5/00* (2006.01)
*A61F 5/01* (2006.01)

(52) U.S. Cl.
CPC .................. *A61F 5/01* (2013.01); *A61F 5/0123* (2013.01); *A61F 2005/0144* (2013.01); *A61F 2005/0148* (2013.01)
USPC ................................... 602/16; 602/23; 602/26

(58) Field of Classification Search
USPC .................. 602/5, 16, 23–28; 128/882; 5/624
See application file for complete search history.

(56) References Cited

U.S. PATENT DOCUMENTS

| 3,823,424 | A | | 7/1974 | May | |
|---|---|---|---|---|---|
| 3,901,223 | A | * | 8/1975 | May | 602/16 |
| 3,976,057 | A | | 8/1976 | Barclay | |
| 4,064,569 | A | | 12/1977 | Campbell | |
| 4,145,766 | A | | 3/1979 | May | |
| 4,523,585 | A | | 6/1985 | Lamb et al. | |
| 4,628,916 | A | * | 12/1986 | Lerman et al. | 602/16 |
| 4,856,501 | A | | 8/1989 | Castillo et al. | |
| 4,911,709 | A | | 3/1990 | Marlow et al. | |
| 5,018,514 | A | | 5/1991 | Grood et al. | |
| 5,259,832 | A | | 11/1993 | Townsend et al. | |

(Continued)

FOREIGN PATENT DOCUMENTS

| AT | 508918 A4 | 5/2011 |
|---|---|---|
| EP | 0297766 A1 | 1/1989 |

(Continued)

OTHER PUBLICATIONS

C.W. Radcliffe, "Four-bar linkage prosthetic knee mechanisms: kinematics, alignment and prescription criteria", Prosthetics and Orthotics International, 1994, vol. 18, pp. 159-173.

(Continued)

*Primary Examiner* — Michael A. Brown
(74) *Attorney, Agent, or Firm* — Workman Nydegger (57) ABSTRACT

A device and method for using the device arranged to maintain anatomical alignment between a joint by creating a dynamic load around the joint to restore and maintain the anatomical alignment. The orthotic device uses a hinge to create a directed force on a tibia by maintaining misalignment of an instant center of rotation (ICoR) of the hinge at a position relative to an anatomical knee joint.

16 Claims, 7 Drawing Sheets

(56) References Cited

U.S. PATENT DOCUMENTS

| | | |
|---|---|---|
| 5,261,871 A | 11/1993 | Greenfield |
| 5,437,611 A | 8/1995 | Stern |
| 5,628,722 A | 5/1997 | Solomonow et al. |
| 5,746,774 A * | 5/1998 | Kramer et al. ............ 623/39 |
| 5,873,847 A | 2/1999 | Bennett et al. |
| 5,954,677 A | 9/1999 | Albrecht et al. |
| 7,044,925 B2 | 5/2006 | Castillo et al. |
| 7,097,627 B2 | 8/2006 | Enzerink et al. |
| 7,192,407 B2 | 3/2007 | Seligman et al. |
| 7,309,322 B2 | 12/2007 | Albrecht et al. |
| 7,435,234 B2 | 10/2008 | Gamada |
| 7,534,217 B2 | 5/2009 | Seligman et al. |
| 7,811,242 B2 | 10/2010 | Seligman |
| 7,846,115 B2 | 12/2010 | Seligman et al. |
| 8,048,013 B2 | 11/2011 | Ingimundarson et al. |
| 2002/0052568 A1 | 5/2002 | Houser et al. |
| 2005/0015156 A1 | 1/2005 | Hikkichi |
| 2007/0270976 A1 | 11/2007 | DeHarde et al. |
| 2009/0124948 A1 | 5/2009 | Ingimundarson et al. |
| 2009/0299244 A1 * | 12/2009 | Chiang et al. ............ 602/26 |
| 2012/0059296 A1 | 3/2012 | Kompa |

FOREIGN PATENT DOCUMENTS

| | | |
|---|---|---|
| EP | 1 114 619 B1 | 12/1999 |
| WO | 2010087899 A2 | 8/2010 |

OTHER PUBLICATIONS

International Search Report from corresponding PCT Application No. PCT/US2012/068343 dated Mar. 19, 2013.

* cited by examiner

FIG. 3A  The tangent method

FIG. 3B  The Reuleaux method

HINGE USED FOR THE TREATMENT OF ANTERIOR AND POSTERIOR CRUCIATE LIGAMENT INJURY AND METHOD FOR USING THE SAME

FIELD OF ART

The present disclosure relates generally to the field of orthopedic devices, and more particularly to an orthotic device having a hinge that misaligns the device to create a dynamic load on a body part.

BACKGROUND

An untreated posterior cruciate ligament (PCL) injury heals sub optimally due to laxity caused from lengthening of the PCL. Since laxity of the PCL leads to instability and injury of a person, PCL devices on the market are used to treat such injuries. These PCL devices generally use hinges that have a traditional 4-bar design, a constant force application design, or a constant resistance application design.

Figure 1A:
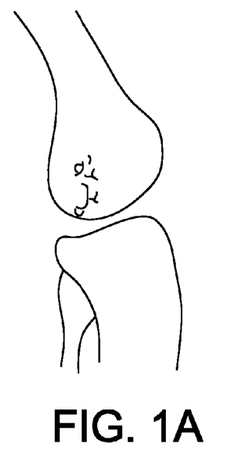
FIG. 1A is an illustrative example of the ends of a tibia and fibula to calculate the theoretical center of rotation for a biological knee.
Figure 1B:
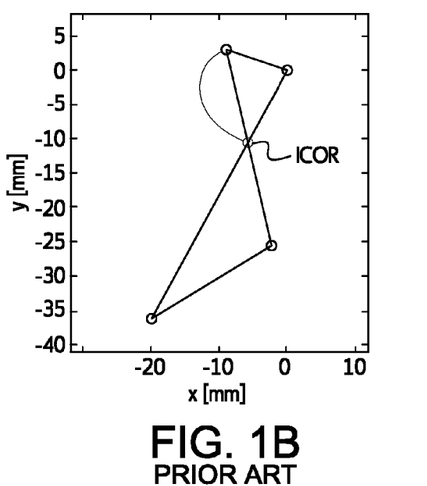
FIG. 1B is a representative graph of the movement of an ICoR of the biological knee and a traditional 4-bar hinge.

The traditional 4-bar design uses a hinge that attempts to closely imitate the instant center of rotation (ICoR) behavior of the biological knee. FIG. 1A illustrates moving ends of the tibia and fibula which can calculate the ICoR of the biological knee. The traditional 4-bar hinge attempts to closely imitate the movement of the biological knee. As seen in FIG. 1B, the movement of ICoR of the biological knee and traditional 4-bar hinge are both relatively stationary, moving only between 10-20 mm. This design is used to avoid device migration and/or pistoning of the device cuff.

Examples of traditional, prior art braces including traditional 4-bar hinges are found in at least: U.S. Pat. No. 4,856,501, granted Aug. 15, 1989, U.S. Pat. No. 7,044,925, granted May 16, 2006, and U.S. Pat. No. 8,048,013, granted Nov. 1, 2011, and U.S. patent application publication 2012/0059296, published Mar. 8, 2012. Each of these documents is incorporated by reference in their entirety.

Figure 2:
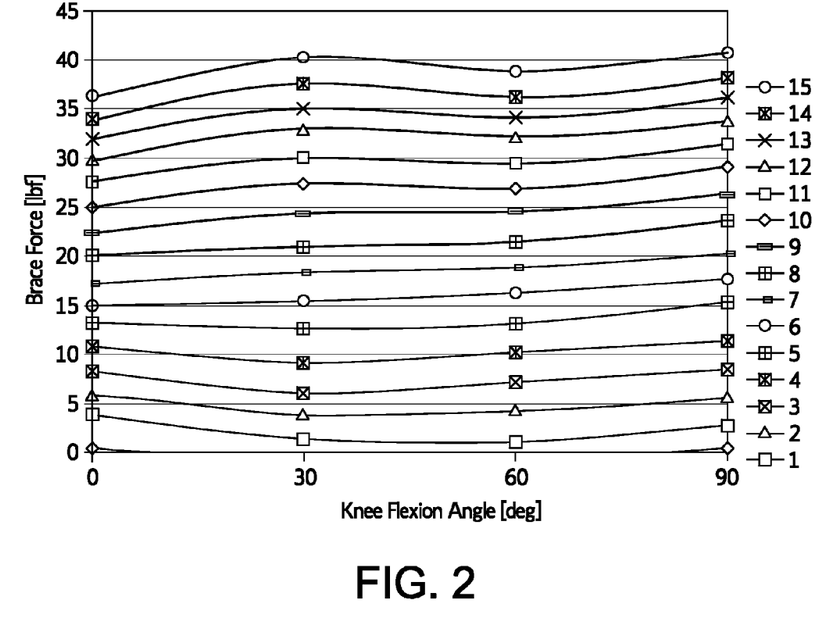
FIG. 2 shows the force generated by a constant force hinge at different knee flexion angles.

A constant force design uses a passive, single axis hinge that connects a femoral cuff to the distal part of the tibial cuff. The proximal end of the tibial cuff can rotate about a pivot point on the distal cuff to allow the pushing of the tibial cuff forward by a spring independent of the movement of the hinge. However, as seen in FIG. 2, the forces exerted by the spring on the proximal tibia are constant regarding flexion angle.

A constant resistance design uses a hinge that provides dampening forces as the knee flexes, to reduce posterior tibial sag by preventing sudden rotation of the knee. However, to flex the knee joint, the patient must exert an extra flexion moment by using the hamstring muscle to load the constant resistance member of the hinge, which causes posterior tibial sag making the device counterproductive.

These known designs, however, are deficient for effectively treating a PCL injury, since these hinges do not prevent the lengthening of the PCL during flexion of the knee. The traditional 4-bar hinge design is only used to track the movement of the biological knee and is not used to provide a dynamic load to supplement the PCL. The constant force and constant resistance hinges only provide constant force and may require the patient to use muscles for leg movement that may lead to the lengthening of the PCL.

In view of these known designs, there is still a need for an orthopedic hinge that provides a dynamic load during flexion and extension of the leg to maintain anatomical alignment of the tibia and fibula to prevent the lengthening of the PCL.

SUMMARY

The present disclosure is directed to a device and method for using the device that satisfies the need to maintain anatomical alignment between a joint by creating a dynamic load around the joint to restore and maintain the anatomical alignment. An example of this device is an orthotic device that uses a hinge to create an anteriorly directed force on the tibia by maintaining an ICoR of the hinge at an inferior position relative to an anatomical knee joint, when treating a PCL injury.

According to an embodiment, the hinge or pair of hinges are located proximate to the knee, and connects upper and lower cuffs. The upper cuff secures to the upper leg, such as over the thigh either the posterior or anterior side, and a lower cuff secures to the lower leg, such as over the shin or calf. Through the ICoR, the lower cuff is arranged and oriented so as to exert the anteriorly directed force from the ICoR onto the lower leg to create a desired anatomical correction.

The hinge has an upper linkage with first and second pivoting ends, a lower linkage with first and second pivoting ends, and first and second upright linkages pivotally connected to the first and second pivoting ends of the upper and lower linkages. The pivotal connections form an ICoR of the hinge located at an inferior position relative to an anatomical knee joint. By maintaining the ICoR of the hinge at an inferior position during flexion and extension of the knee, the hinge attempts to realign a lower tibial cuff of the device, which creates an anteriorly directed force on the tibia. This force generated by the realignment of the device helps unload the PCL at increased flexion angles.

Another example of this device is an orthotic device that uses a hinge to create a posteriorly directed force on the tibia by maintaining an ICoR of the hinge at a superior position relative to the anatomical knee joint. By maintaining the ICoR of the hinge at a superior position during flexion and extension of the knee, the device that uses this hinge attempts to realign the lower tibial cuff, but instead, creates a posteriorly directed force on the tibia to effectively unload the anterior cruciate ligament (ACL) at decreased flexion angles.

From the embodiments herein, the linkages of the hinge on the brace are manipulated to achieve a pattern of movement of an upper or first cuff relative to a lower or second cuff of the device connected to one another by the hinge. The desired relative displacement between the upper and lower cuffs is matched to the hinge, through orientation of the linkages of the hinge, which mimics the displacement to generate specific a load to match the desired anatomical correction or movement; for example shifting of the tibia a minimum of 1 mm, and more specifically 3 mm anteriorly by the load during flexion of the knee. The desired shifting may vary from patient to patient, in that for one patient the shift may be 3 mm whereas for another patient having different anatomical proportions the shift may be 5 mm. It is through the ICoR that the hinge pushes the cuffs to generate the load for such anatomical correction.

Methods may be employed to treat injuries of the PCL and ACL using any of the embodiments of the orthotic devices having the hinges described above, in a dynamic manner through extension and flexion of a knee.

The numerous advantages, features and functions of the embodiments will become readily apparent and better understood in view of the following description and accompanying drawings. The following description is not intended to limit the scope of the device, hinge and method for using the same, but instead merely provides exemplary embodiments for ease of understanding.

BRIEF DESCRIPTION OF THE DRAWINGS

Examples of a device having a hinge designed according to different embodiments of the present disclosure will now be explained in more detail referring to the drawings.

In the various figures, similar elements are provided with similar reference numbers. The drawing figures are not necessarily drawn to scale, or proportion, but instead are drawn to provide a better understanding of the components, and are not intended to be limiting in scope, but rather provide exemplary illustrations.

DETAILED DESCRIPTION OF VARIOUS EMBODIMENTS

A. Overview

There are approximately 200,000 knee injuries to the ACL, PCL, and combination of ACL and PCL injuries sustained by people every year. Of these injuries, approximately 10% of the knee injuries are to the PCL.

In a healthy knee, the cruciate ligaments, i.e., the PCL and ACL, help stabilize the knee. The ACL prevents an anterior translation of the tibia regarding the femur, while the PCL helps prevent the posterior translation of the tibia regarding the femur. If the ligaments are healthy, the healthy knee will demonstrate little or no subluxation, i.e., dislocation, from the bending and extending of the knee.

Approximately 50% of ACL injuries are repaired since the ACL is found within a capsule of the knee and cannot heal. A fewer amount of PCL injuries are surgically repaired, since the PCL is extracapsular and able to spontaneously heal post injury. However, if the PCL may heal untreated, the PCL may heal less optimally.

While there are many other structural elements in the knee, e.g., the meniscus, to help prevent the posterior translation of the tibia regarding the femur, the majority of force associated with the posterior translation of the tibia is absorbed by the PCL. When the PCL is injured, the PCL can lengthen during the healing process due to strain caused by a posterior shifting of a proximal end of a tibia. The lengthening of the PCL creates a slack in the healed knee, and may further allow the proximal end of the tibia to continually shift posteriorly after the healing process which can cause a feeling of instability in a patient and increase the risk of injury.

A knee having a PCL deficiency will experience different degrees of subluxation, based on the severity of the PCL injury. The severity of the PCL laxity/deficiency can be diagnosed using a standard test, i.e., the posterior drawer test, in which the patient flexes to 90 degree flexion, and the physician applies a posterior force to the anterior proximal tibia.

These tests are used to determine the severity of the PCL laxity/deficiency, which are categorized by a 1 to 3 grading. A grade 1 PCL injury is essentially a light sprain, where the fibers of the PCL have been slightly torn. The grade 1 PCL deficient knee demonstrates a slight posterior subluxation.

A grade 2 PCL injury is a more severe sprain, with the fibers of the PCL are greatly torn, but the PCL is still whole, i.e., the PCL does not have separated fibers. A grade 3 PCL injury is a full tear of the PCL. Although a grade 3 PCL injury may heal, the PCL will likely become excessively long from the posterior shift of the tibia which may cause laxity in the PCL, as discussed above.

Based on the severity of the PCL injury, the PCL deficient knee will have varying degrees of subluxation. While a knee having an ACL injury requires a posteriorly directed force on the proximal tibia to enhance stabilization and reduce tension on the ACL, a knee having a PCL injury requires an anteriorly directed force on a posterior side of the proximal tibia as the knee flexes. By providing support to the posterior of the proximal tibia at different degrees of flexion, the subluxation, i.e., unwanted shifting can be prevented. By preventing the unwanted shift of the tibia, the lengthening of the PCL during healing may be prevented to offer added stability to the patient and a decreased risk of injury.

In viewing the design of the hinge that supplements the PCL, we first look at the rotational motion of a healthy knee. As it is well known, the knee joint is not a single axis joint. The tibia does not rotate about a single, stationary axis regarding the femur, but instead, the tibia rotates about a moving axis.

The moving axis of the knee joint is called the instant center of rotation (ICoR), i.e., the center of rotation at any instance such as any flexion angle or time. This movement, e.g., translational and rotational movement, of the ICoR is not a wild movement, but rather the ICoR only moves within a relatively small circle within the femoral condyles regarding the tibia and does not travel far from the rotating body, i.e., the tibia.

Figure 3A:
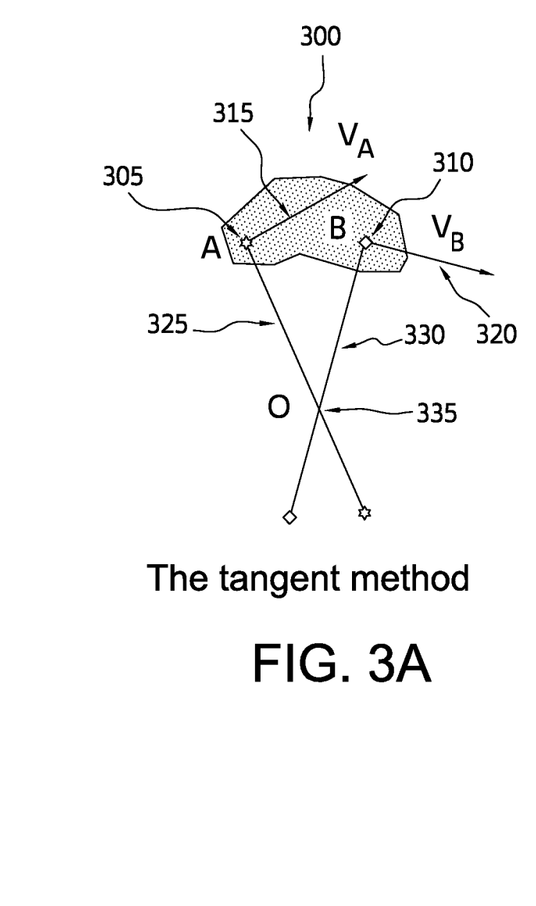
FIGS. 3A and 3B illustrate two methods for locating an ICoR of a moving body.
Figure 3B:
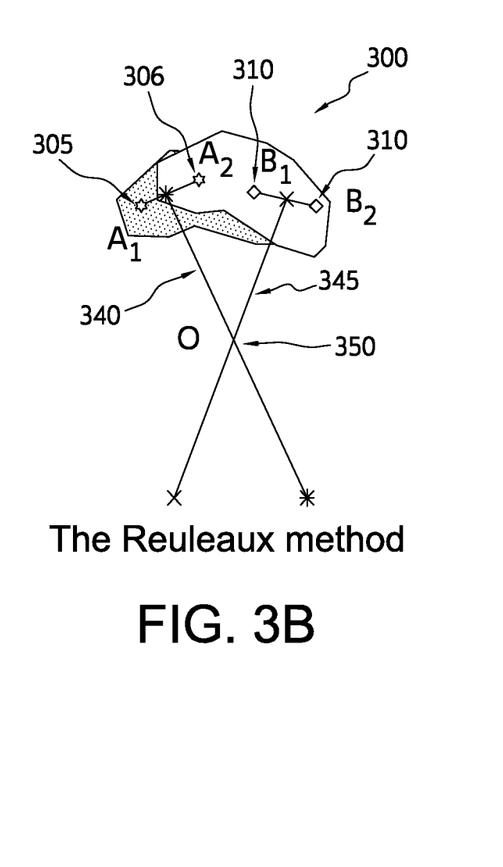

As seen in FIGS. 3A and 3B, there are two methods to find the ICoR of a knee, i.e., the tangent method and the Reuleaux method.

FIG. 3A illustrates that the tangent method considers two points 305, 310 on the rotating body 300. As the name implies, the tangents of these two points 305, 310 are found, i.e., the directional vectors of their movement 315, 320. Perpendicular lines 325, 330 are then drawn through each of the points 305, 310 perpendicular to the tangent lines 315, 320 respectively. The ICoR of the moving body 300 is determined from the point of intersection 335 of the two perpendicular lines 325, 330.

The Reuleaux method uses the same points 305, 310 as used in the tangent method but considers the points at two separate instances 306, 311, for example, at two flexion angles at a first time 305 and a second time 306. A line is then drawn between points 305 and 306 and between 310 and 311 at the different instances, from which perpendicular lines 340, 345 are drawn from the middle of the connecting line. The ICoR of the moving body 300 is then determined from the point of intersection 350 of the two perpendicular lines 340, 345. As the difference in flexion angle of the moving body approaches zero, the Reuleaux method converges into the tangent method.

Determining the location of the ICoR is a key element in understanding the movement of a rotating body and forces that result from the movement during flexion and extension, since the distance of the ICoR from the rotating body determines the relationship between rotational and translational movement. When a body moves along a circle with a small radius, a greater rotational movement will result. Whereas, the body moving along a circle having a greater radius will cause greater translational movement.

The design of most hinges for orthopedic knee devices attempts to imitate the movement of the ICoR of a healthy knee by incorporating both rotational and translational movement during flexion and extension of the knee, i.e., keeping the ICoR at the same distance from the moving bodies. Incorporating the movement in the hinge axis attempts to create perfect alignment with the anatomical axis of the joint so no movement takes place between the hinge and the joint, to replicate the natural movement.

If the axes are not ideally placed to coincide with the anatomical axis of the joint, during movement of the leg forces will act to relocate the hinge to coincide with the anatomical axis of the knee joint, which will create a pressure on the skin or even produce migration issues regarding the device. The relocation effort of the hinge is generally due to horizontal misalignment and vertical misalignment of the hinge axis. In this discussion, the term "vertical" is defined as a direction along the tibial axis, while the term "horizontal" is defined as a direction perpendicular to the tibial axis in the sagittal plane. It should be kept in mind that the terms vertical and horizontal are relative to corresponding leg, and not necessarily in a fixed Cartesian space.

Vertical misalignment generally occurs in two ways, i.e., excessive vertical translation and insufficient vertical translation during flexion and extension. When a hinge has a single axis, there is insufficient vertical displacement in the device due to the limited motion of the ICoR of the hinge axis. This limited motion causes a vertical misalignment from the forces acting on the device to seek realignment of the hinge by moving and end of either the tibial cuff or the femoral cuff closer to the anatomical axis of the knee joint.

While a hinge having a multi-link system can have excessive vertical displacement due to the ICoR of the hinge traveling either too far anteriorly or too far posteriorly regarding the tibial axis during knee flexion and extension. This displacement creates forces in the hinge to reposition either the tibial cuff or the femoral cuff, which is called "pistoning." In both cases of vertical displacement, the repositioning of the cuff of the device causes stress at the cuff-skin interface and can lead to discomfort, skin irritation, and device migration.

Horizontal misalignment can occur due to excessive and insufficient horizontal translation during movement of the knee joint. Similar to the vertical misalignment in the single axis hinge, insufficient horizontal displacement occurs in the single axis hinge when a lack of motion of the ICoR causes horizontal misalignment. Excessive horizontal displacement can occur in a multilink system when the ICoR of the hinge travels too far superiorly or too far inferiorly along the tibial axis depending on the anatomical position of the knee.

Horizontal misalignment causes the device to apply pressure to both the tibia and femur. When a device has four points of leverage, all four points are active in applying the load to the body. This load is compensated by the patient's soft tissue and the soft goods of the device as the ICoR of the hinge shifts towards the anatomical axis of the knee joint.

In another example to understand the effect of a shifting ICoR of the hinge in relation to a moving body, the tibial cuff of the device is identified as the moving body, while the femoral cuff is stationary. Three preferred movements are discussed below. In these descriptions, the tibial axis is the axis that runs through the length of the tibia.

The first movement analyzed is the motion created along the tibial axis to generate cuff pistoning. To create this motion along the tibial axis, the ICoR should be positioned far away from the hinge and oriented such that the radius of the motion is close to a perpendicular axis to the tibial axis, i.e., the ICoR is located more posterior or more anterior than the anatomical knee joint.

The second movement analyzed is the motion to create rotation with minimal translation. This motion to minimize translation is created by locating the ICoR close to the moving body. By orienting the ICoR in such a way, translational movement is minimized for each degree of rotation.

The third movement analyzed is the motion used to create a motion perpendicular to the tibial axis to generate load on the tibia due to misalignment. This translational movement perpendicular to the tibial axis, i.e., the sagittal plane, is created by positioning the ICoR far away from the hinge, and oriented such that the radius of motion is close to the tibial axis, i.e., the ICoR is located more superiorly or more inferiorly regarding the tibia depending on the anatomical position of the knee. Therefore, when the knee is flexed, force can be generated on the posterior side of the proximal tibia.

B. Discussion of Various Embodiments

As generally discussed above, by understanding the movement of the ICoR of a hinge during different movements of body parts, a device can be designed that generates forces to supplement and support an injured ligament during these movements. A knee device can be designed having a hinge that shifts a calf cuff of the device regarding a thigh cuff by creating forces to realign the device, i.e., creating a "smart" misalignment of the ICoR of the hinge. This "smart" misalignment, or "beneficial" realignment, creates pressure on the tibia at different ranges of motion of the knee by having the ICoR of the hinge positioned either too far posteriorly or too far anteriorly regarding the tibia to unload an injured PCL or ACL by restoring and maintaining anatomical alignment of the tibia and fibula.

If the device is aligned too far posteriorly, a posteriorly directed force is generated at different knee angles on the anterior proximal tibia, and/or an anteriorly directed force is generated on the posterior of the distal femur. The anterior proximal femur would experience a posteriorly directed force, while the posterior distal tibia would experience an anteriorly directed force. This type of misalignment results in the proximal tibia being pushed posteriorly regarding the distal femur. Although this force would put an additional load on the PCL, the force may be helpful in reducing the load on the ACL.

If the device is aligned too far anteriorly, the direction of the forces on the tibia and femur would be reversed. In this configuration, the posterior proximal tibia and posterior proximal femur would each experience an anteriorly directed load, while the anterior distal tibia and the anterior distal femur would experience a posteriorly directed force. This would cause the proximal tibia being pushed anteriorly regarding the distal femur, which would reduce the load on the PCL.

In one embodiment of the present disclosure, an orthotic device having a hinge that creates an increasing dynamic load on the user's tibia is provided. In this embodiment, it was unexpectedly found that a hinge having a four-bar hinge design could support an injured PCL by preventing unwanted shifting of the tibia regarding a femur during the bending and extension of a knee, i.e., throughout various ranges of motion of the knee by creating anteriorly directed forces.

The four-bar hinge provides supplemental forces to a tibia of a user by dynamically misaligning a tibial cuff of the device anteriorly when the knee is bent, i.e., at varying degrees of knee flexion, to generate an anteriorly directed force on a posterior of the tibia by maintaining the ICoR of the hinge inferiorly regarding the anatomical knee joint. During knee flexion and extension, the linkages of the four-bar hinge creates a shift in the calf cuff regarding the thigh cuff creating an anteriorly directed force to restore and maintain anatomical alignment of the tibia and fibula.

This configuration of the hinge exploits a joint center at a point of flexion. As the wearer of the device moves his or her knee between flexion and extension, the ICoR of the hinge shifts to a position inferior to the anatomical knee joint axis to create a misalignment of the ICoR of the hinge regarding the anatomical knee joint depending on the angle of flexion. This lack of congruence of these axes creates an open chain biomechanical force on the anatomical joint as the two axes attempts to coincide with one another. As the flexion angle increases, a greater amount of force will be generated due to the greater misalignment of the ICoR of the hinge to provide greater support to an injured PCL.

Figure 4A:
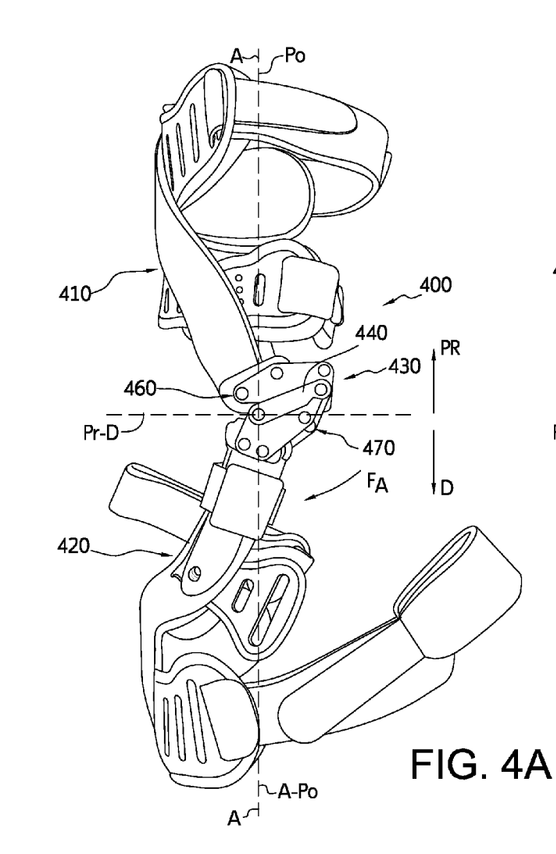
FIGS. 4A and 4B shows a first exemplary embodiment of a device having a hinge having the features of the present disclosure that generates an anteriorly directed force by maintaining an inferior position regarding an anatomical knee joint.
Figure 4B:
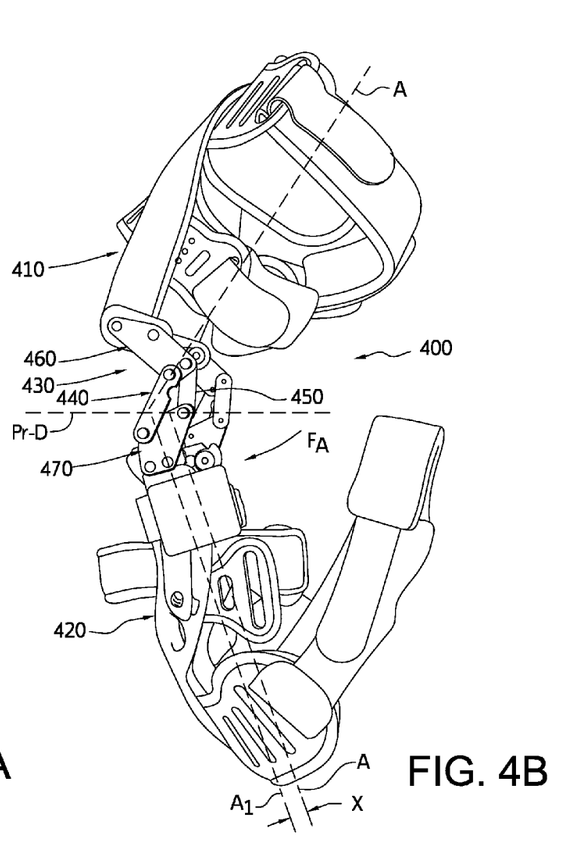
Figure 5A:
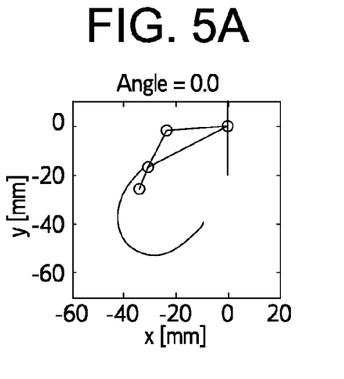
FIGS. 5A-5F are illustrative graph showing the movement of the linkages of the hinge and ICoR at various degrees of flexion.
Figure 5B:
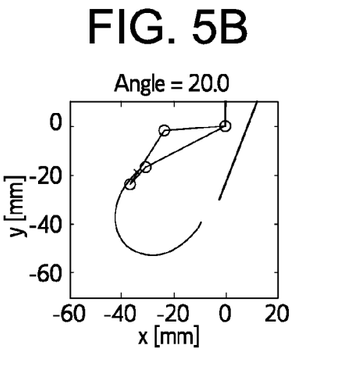
Figure 5C:
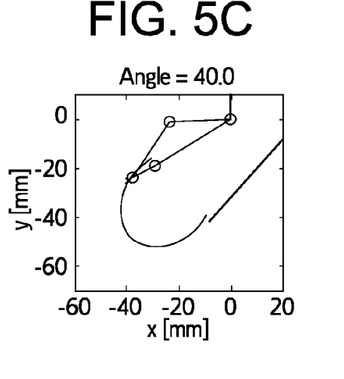
Figure 5D:
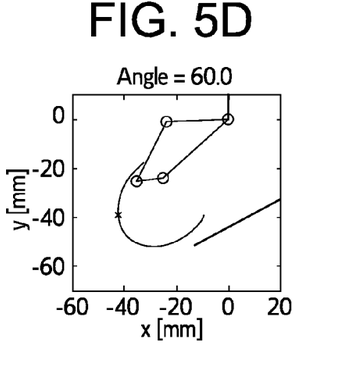
Figure 5E:
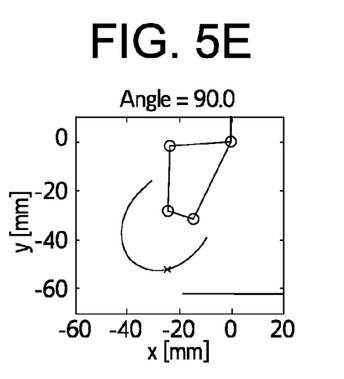
Figure 5F:
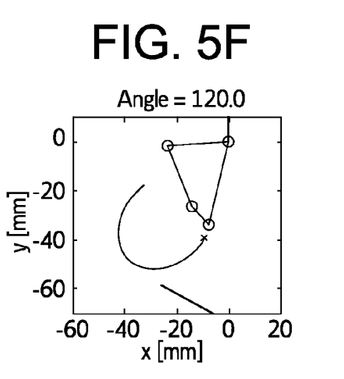

FIGS. 4A and 4B illustrate an embodiment of the orthotic device having the proposed hinge design that maintains the ICoR of the hinge in an inferior position regarding the anatomical knee joint throughout various knee angles.

For explanatory purposes, the orthotic device may be divided into sections which are denoted by general anatomical terms for the human body. Each of these terms is used in reference to a human leg and knee joint divided in similar sections with a proximal-distal plane (Pr.-D) generally extending along a meniscus of a knee between the femur and tibia. The orthotic device is also divided into anterior and posterior sections by an anterior-posterior plane (A-Po). The anterior-posterior plane generally corresponds to the coronal or frontal plane of a human leg. Each of the anterior and posterior sections may be further divided about the center of the knee by a proximal-distal plane and a lateral-medial plane. The proximal-distal plane and the anterior-posterior plane generally correspond to an anatomical axis of a knee joint when the orthotic device is worn.

Device 400 is made from a rigid material, such as, plastic, metal, composite fiber, carbon fiber, etc., to provide proper support to the leg of the wearer. The device 400 has an upper femoral cuff 410 and lower tibial cuff 420 connected by hinge 430. The device 400 can also have features that are generally well known in the art, for example, padded supports connected to the upper femoral cuff 410 and lower tibial cuff 420 and positioning/tensioning straps connected to the cuffs 410, 420 to wrap and position the device 400 around the leg of a wearer. The padded supports and straps can be made from materials well known in the art to provide a comfortable and secure attachment of the device 400, e.g., the positioning/tensioning straps can be made from an elastic or non-elastic fabric and the padded supports can be made from neoprene, foamed polyurethane, or similar support.

Hinge 430 includes two upright linkages 440, 450 connected with upper linkage 460 and lower linkage 470. The upper linkage 460 and lower linkage 470 are connected to the upper femoral cuff 410 and lower tibial cuff 420, respectively, by a connecting element, for example, rivet, screw, button, or similar linking element. The two upright linkages 440, 450 are pivotally connected to the upper linkage 460 and lower linkage 470 by a similar pivotable linking element to allow the re-positioning of the ICoR of the hinge by the folding of the upright linkages 440, 450. The hinge 430 and linkages can be made from a rigid metal, hard plastic or similar material that allows transferring force generated by the repositioning of the ICoR of the hinge to the lower tibial cuff 420 without bending, breaking, or similar failure.

For example, as seen in FIG. 4A, when the device 400 in a fully extended or extension position, i.e., at a 0 degree flexion angle, the ICoR of the hinge 430, i.e., the intersection of the two upright linkages 440 and 450, is in a proximal position regarding the anatomical axis of the knee joint. In this state, the ICoR of the hinge 430 is aligned regarding the anatomical knee joint creating an anteriorly directed force $F_A$ to shift the tibial cuff 420 regarding the upper femoral cuff 410 to maintain proper alignment of the tibia and fibula. At these low angles, however, the hinge generates a lower amount of force than generated by a hinge at a higher angle of knee flexion, since the injured PCL needs little support near full extension.

For example, there may be an anterior shifting of the tibia at a minimum of 1 mm by the load applied by the lower cuff during flexion of the knee. The desired shifting may vary from patient to patient, in that for one patient the shift may be 3 mm whereas for another patient having different anatomical proportions the shift may be 5 mm. The orientation and placement of the linkages are arranged accordingly.

As schematically exemplified in a simplified manner in FIG. 4B, the relative shift X of the upper cuff to the lower cuff is from an axis A-A (such as, but not specifically, an axis generally defined along the anterior-posterior plane (A-Po) in FIG. 4A) to when the device is in extension to an axis $A_1$-$A_1$ when the device is in flexion with the lower cuff shifting relative to the axis A-A. The axis A-A may be treated to correspond to both the upper and lower cuffs as they articulate, respectively, and the shift from axis A-A is represented as being from what the lower cuff would have been but for the orientation and placement of the linkages to cause the displacement of the lower cuff relative to the upper cuff.

When the knee is flexed in flexion (full flexion being at least 90 degrees), as shown in FIG. 4B, the intersection between the two upright linkages 440 and 450, shifts the ICoR of the hinge inferiorly away from the anatomical axis of the knee joint, which generates anteriorly directed forces $F_A$ on the tibial cuff 420 to shift the lower tibial cuff regarding the upper femoral cuff. As the knee angle increases, a greater amount of force is generated by the greater misalignment of the ICoR of the hinge away from the anatomical motion of the knee. The shift, therefore, generates a greater anteriorly directed force on the posterior of the proximal tibia to provide added posterior support to the tibia to align the proximal tibia anteriorly than the anteriorly directed force generated at a lower flexion angle, as discussed above.

The ICoR of the hinge determines the motion of the lower linkage 470 on the lower tibial cuff regarding the upper linkage 460 on the upper femoral cuff. By deviating the motion of the lower linkage 470 regarding the upper linkage 460 from the anatomical motion, a misalignment is created between the device and the leg. The misalignment is such that as the knee angle increases, the lower linkage 470 moves further anteriorly than expected from the anatomical motion to cause an anteriorly directed force on the calf.

As seen in the following paragraphs, it was unexpectedly found that using a hinge that has a shifting ICoR with respect to regarding the anatomical knee joint could generate similar forces created by a healthy PCL based on the distance of the ICoR of the hinge from the anatomical knee joint.

The ICoR of the hinge has a shifting ICoR curve starting in a position adjacent to the anatomical axis of a knee joint and move farther away, i.e., typically in a range of about 10 to about 15 cm, from the hinge to a inferior position with respect to regarding the anatomical knee joint when the device moves from a 0 degree flexion angle (extension) to about a 90 degree flexion angle.

The greater traveling distance of the ICoR of the hinge, as presented in this disclosure, generates a greater anteriorly directed force on the posterior side of the proximal tibia at various flexion angles due to this greater inferior movement of the ICoR of the hinge than the traditional 4-bar hinge. By aligning the hinge at the level of the anatomical axis at full extension and using the mismatch between the anatomical ICoR and the hinge ICoR described above to misalign the hinge as the hinge and knee joint flex, the hinge axis moves to a position posterior to the anatomical knee axis generating a force to move anteriorly to locate itself over the anatomical axis. This greater generation of force is exploited through the linkages of the hinge to create stabilizing biomechanical forces at various flexion angles of the knee; effectively unloading an injured PCL.

Figure 6:
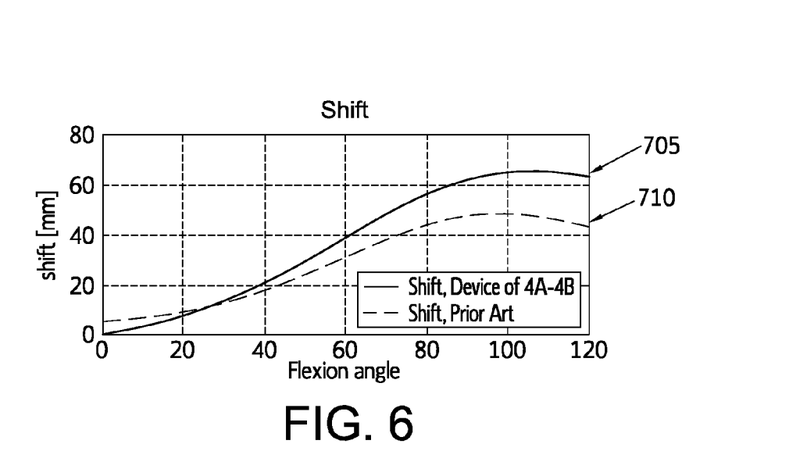
FIG. 6 is an illustrative graph showing a shift in the ICoR of the hinge having the features of the present disclosure relative to a traditional 4-bar hinge.

The geometry of the ICoR of the hinge 430 is further illustrated in FIGS. 5A-5F. As seen in these figures, the ICoR of the hinge moves to shift the linkages of the hinge 430 at different flexion angles. FIG. 6 illustrates the shift data taken and plotted at the flexion angles to determine the shift generated by the movement of the linkages. Shift curve 705 of the hinge having the proposed design has a greater amount of shift than the shift curve of a traditional 4-bar hinge seen in shift curve 710. By positioning the ICoR of the hinge inferiorly regarding the anatomical axis, forces are generated on the anterior thigh while the ICoR of the hinge shifts inferiorly to create an increased load on the posterior of the tibia.

The shifting of the ICoR of the hinge at various flexion angles maintains the shape of the movement of the curve since the knee joint itself also has a moving center of rotation as compared to a traditional 4-bar hinge design. The misalignment of the hinge is achieved using different geometries of the hinge based on the shape of the ICoR curve. Regardless of the geometry of the hinge, however, the force on the tibia is generated from the inferior movement of the ICoR of the hinge based on the shape of the ICoR curve. To properly generate this force, the ICoR of the curve should start proximally to the joint center, move inferiorly to create the shift of the ICoR, and then return towards the joint center so as not to increase the misalignment beyond about a 90 degree flexion angle. Alternatively, one having ordinary skill in the art appreciates that the ICoR curve of a hinge does not have to return towards the joint center, so an increasing force is generated beyond a 90 degree flexion angle, depending on the injury to be treated.

Figure 7:
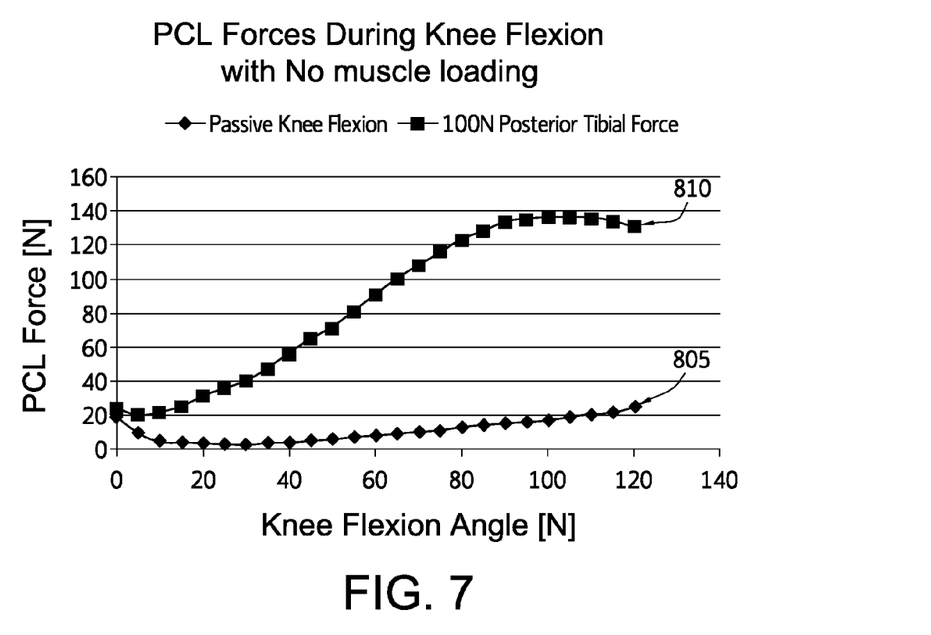
FIG. 7 is an illustrative graph showing a loading of a PCL at different flexion angles.

As illustrated in FIG. 7, the variable loading of the healthy PCL is seen throughout various ranges of motion of the knee. As seen in the passive knee flexion curve 805, the PCL does not generate a considerable amount of force around the knee during different flexion angles. A greater amount of force, however, is generated by the PCL on the tibia with a 100 Newton loaded force on a posterior side of the tibia, which is illustrated by the 100 N posterior tibial force curve 810. For example, at 0-20 degree flexion of the knee, the PCL is not loaded, but as the flexion angle increases, the force on the PCL loads. The loading of the PCL gradually increases as the knee flexes and reaches a maximum force at about 100 degree flexion angle. It is understood, that a healthy PCL provides a posteriorly directed force by pulling on the posterior of the proximal femur or provides an anteriorly directed force by pulling the posterior of the proximal tibia, mostly during flexion of the knee.

When comparing the shift curve 705 of FIGS. 5A-5F, 6 with the loading curve 810 in FIG. 7, it was unexpectedly found that the shape of the shift curve was almost identical to the loading curve by the healthy PCL on the tibia. The shape of the misalignment is almost identical to the forces in the PCL throughout the range of motion.

Therefore, the hinge having the ICoR that shifts inferiorly regarding the anatomical knee joint causes a displacement of the lower tibial cuff with respect to regarding the upper femoral cuff to provide an anteriorly directed force on the proximal posterior tibia when the knee is bent to effectively replicate the energy loading of the healthy PCL. The device having this hinge unloads the wearer's PCL by shifting the calf cuff regarding the thigh cuff to provide proper support and stability for the injured PCL by restoring and maintaining anatomical alignment of the tibia and fibula.

Figure 8:
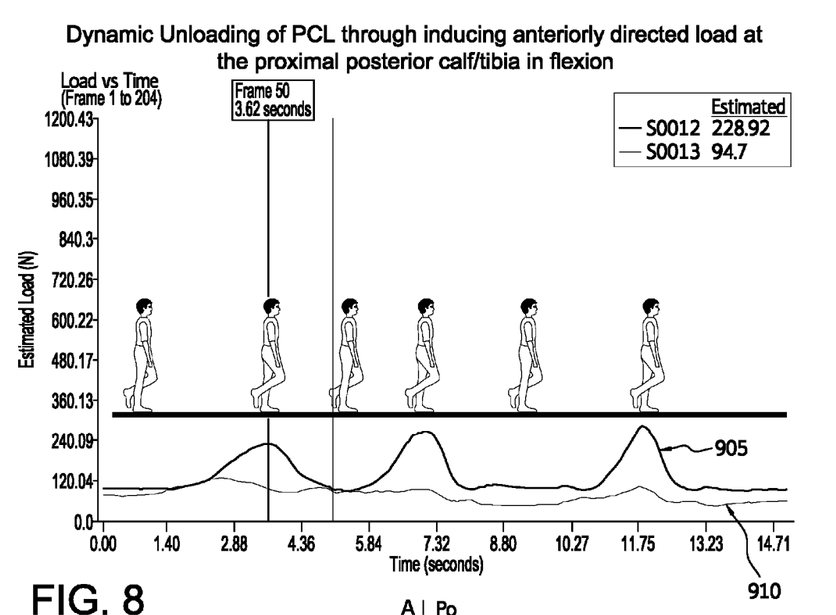
FIG. 8 is an illustrative graph showing a dynamic unloading of the PCL by the hinge during a gait cycle of a wearer.

To get a shift curve that resembles the loading curve of the PCL as seen in FIG. 8, the ICoR of the hinge must be located proximally for the first 20 degrees of flexion. When the hinge flexes beyond 20 degrees, the ICoR of the hinge moves inferiorly, to create horizontal misalignment so the tibial cuff is located more anteriorly than the tibia.

When the device 400 has an increased flexion angle, the hinge 430 generates a greater force on a posterior side of the proximal tibia by shifting the ICoR of hinge inferiorly regarding the anatomical motion of the knee joint. As the knee continues to flex, the ICoR of the hinge moves further inferiorly to create a greater misalignment with respect to regarding the anatomical knee joint. When the knee reaches about a 90 degree flexion angle, the ICoR returns to a more proximal position to maintain the misalignment of the ICoR regarding the anatomical axis of the knee joint and does not increase as the knee flexes beyond 90 degrees.

FIG. 8 further provides evidence of the unexpected load created by misaligning the ICoR of the hinge with respect to regarding the anatomical axis of the knee joint. As shown in FIG. 8, when the device having the hinge, is worn by a user on the right leg, a greater dynamic unloading of the PCL is provided during a gait cycle. As the user provides a greater flexion angle during the gait cycle, a greater amount of unloading is provided, as seen in unloading curve 905, by the hinge due to the increased shift of the ICoR of the hinge from the anatomical knee joint.

The different embodiments of the hinge discussed above use the misalignment of the ICoR of the hinge to generate forces on the proximal posterior tibia and the distal anterior femur to prevent posterior subluxation of the tibia, i.e., restore and/or maintain anatomical alignment of the tibia and the fibula. This would then effectively supplement the action of a healthy PCL by having the device provide varying loads to the tibia to mirror the loading behavior of the healthy PCL. This added support may prevent a lengthening of the PCL during the healing process and prevent shifting problems to give a wearer an added feeling of stability and a decreased risk of injury.

One having ordinary skill in the art can appreciate that the positioning of the ICoR of the hinge regarding the anatomical axis can be altered to treat different knee injuries or provide different supporting forces on a knee by a device using the hinge. For example, as discussed above, the As ICoR of the hinge can move superiorly with respect to regarding the anatomical axis of the knee joint to treat a knee having an ACL injury. In this case, the positioning of the ICoR of the hinge is used to create a posteriorly directed force on the proximal anterior tibia to supplement an injured ACL during knee extension.

Figure 9:
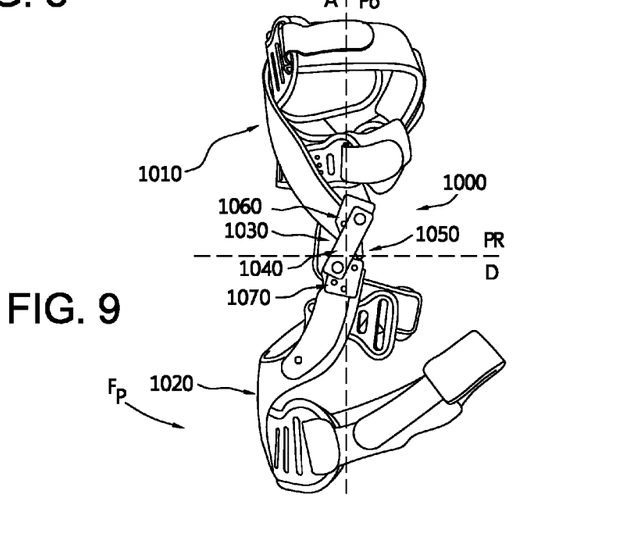
FIG. 9 shows another embodiment of a hinge having the features of the present disclosure that generates a posteriorly directed force on the tibia.

FIG. 9 shows device 1000 having hinge 1030 that creates a greater posteriorly directed force $F_p$ near full extension, i.e., zero degree flexion, than at ninety degree flexion. Hinge 1030 is constructed similarly to hinge 430 and is pivotally connected to upright linkages 1040, 1050, and connects the upper femoral cuff 1010 to the lower tibial cuff 1020. Hinge 1030, however, has an ICoR that moves further superiorly with respect to regarding the anatomical knee joint as the knee reaches full extension to provide greater support to an injured ACL. The force generated by the movement of the ICoR causes a shift of the lower tibial cuff 1020 posteriorly during extension. This creates an increasing dynamic load in front of the tibia which effectively unloads the ACL, protecting it from undue tension.

An adjustable hinge can be designed that can create either a posteriorly or anteriorly directed force on the device by allowing the re-positioning of the ICoR of the hinge. By allowing such an adjustment of the linkages, the directed forces can selectively treat an injury so that during flexion and extension movements of the knee the anatomical alignment of the tibia and fibula can be restored and maintained.

Figure 10A:
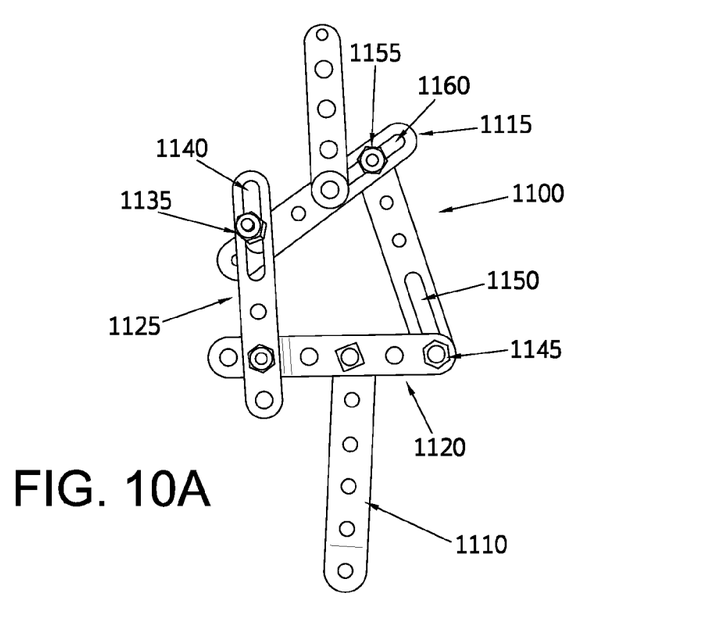
FIGS. 10A and 10B show another embodiment of a hinge having the features of the present disclosure adjustable for a device in an extended and flexed position.
Figure 10B:
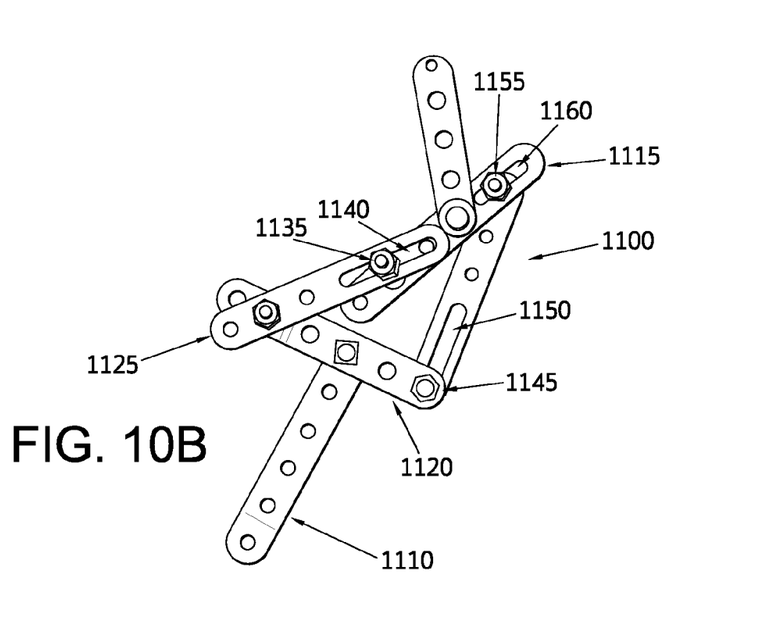

As seen in FIGS. 10A and 10B, an adjustable 4-bar linkage hinge provides an anteriorly directed force on a posterior side of a proximal tibia. Hinge 1100 has an upper femoral connection linkage 1105 and lower tibial connection linkage 1110. The upper femoral connection linkage 1105 has one end connected to an upper linkage 1115, while the other end is connected to a femoral cuff of a device (not shown). The lower tibial connection linkage 1110 has one end connected to a lower linkage 1120 and the other end connected to a tibial cuff of the device of any type shown and known in the prior art. A first upright linkage 1125 is pivotally connected to the upper linkage 1115 and lower linkage 1120 on a first side of the hinge 1100. A second upright linkage 1130 is then connected to the upper linkage 1115 and lower linkage 1120 on a second side of hinge 1100.

As shown in FIG. 10B, by having this configuration, the hinge 1100 can collapse from a first position having a polygonal shape to a second position where a corner formed from the intersection of the upper linkage 1115 and first upright linkage 1125 shifts to fold behind the lower linkage 1120 and second upright linkage 1130. By having the pivot points on the linkages 1125 and 1130 adjustable on the upper linkage 1115 and lower linkage 1120, the ICoR of the hinge can be adjusted to treat various knee injuries.

The adjustment of the hinge 1100 can be accomplished by using an adjustable screw and nut 1135 that connects the first upright linkage 1125 in groove 1140 in different lateral and vertical positions relative to upper linkage 1115. Similarly, the second upright linkage 1130 has a screw and nut 1145 that allows the adjustment of the second upright linkage 1130 regarding the lower linkage 1120 within groove 1150. The upper linkage 1115 also has a screw and nut 1155 that allows the adjustment of the second upright linkage with respect to regarding the upper linkage 1115 within groove 1160.

One having ordinary skill in the art would appreciate that the adjustment of the linkages is not limited to a screw and nut adjustable within a groove, but the adjustment can be accomplished by other well known means in the art. A slidable pin can position the linkages in different positions by being slid into slots along the linkages.

While the foregoing embodiments have been described and shown, alternatives and modifications of these embodiments, such as those suggested by others, may be made to fall within the scope of the disclosure. Any of the principles described may be extended to any other orthopedic devices or other types of articles requiring similar functions of those structural elements described.

The invention claimed is:

1. An orthotic device having a first and second cuffs connected to one another by an articulating hinge between first and second positions, the orthotic device defining a proximal-distal plane, and an anterior-posterior plane intersecting one another to form an intersection axis, the hinge comprising:
   an upper linkage having first and second pivoting ends;
   a lower linkage having first and second pivoting ends; and
   first and second upright linkages pivotally connected to the first and second pivoting ends of the upper and lower linkages,
   the pivotal connection of the first and second upright linkages forming an instant center of rotation (ICoR) located at an inferior position on the posterior side of the anterior-posterior plane, and urging a force directed through the second cuff due to a relative displacement of the first cuff relative to the second cuff which increases as the orthotic device approaches full flexion wherein the ICoR is always located at an inferior position relative to an anatomical knee joint during flexion and extension, wherein said second cuff shifts relative to the first cuff in either a posteriorly or anteriorly direction at least 1 mm from an axis along which the first and second cuffs extend in the second position, relative to when the first and second cuffs extend in a first position.

2. The orthotic device according to claim 1, wherein the first and second upright linkages are pivotally connected by a linking element selected from the group consisting of rivet, bolt, screw, or button.

3. The orthotic device according to claim 1, wherein the first upright linkage is pivotally connected to the first pivoting ends of the upper and lower linkages and the second upright linkage is pivotally connected to the second pivoting ends of the upper and lower linkages.

4. The orthotic device according to claim 1, wherein the first upright linkage is pivotally connected to the first pivoting end of the upper linkage and the second pivoting end of the lower linkage and the second upright linkage is pivotally connected to the second pivoting end of the upper linkage and the first pivoting end of the lower linkage.

5. The orthotic device according to claim 1, wherein the ICoR of the hinge shifts a greater distance at a greater flexion angle during flexion of an anatomical knee joint.

6. The orthotic device according to claim 1, wherein the pivotal connection between the upper linkage and the first upright linkage and the second upright linkage is adjustable.

7. The orthotic device according to claim 1, wherein the pivotal connection between the lower linkage and the first upright linkage and the second upright linkage is adjustable.

8. The orthotic device according to claim 1, wherein in extension, the upper linkage is generally located on the proximal side of the proximal-distal plane.

9. The orthotic device according to claim 1, wherein in extension, the upper linkage folds over the lower linkage.

10. The orthotic device according to claim 1, wherein in flexion, the lower linkage moves anteriorly to form an anteriorly directed force.

11. The orthotic device according to claim 1, wherein in extension, the hinge is misaligned in regard to the intersection axis.

12. The orthotic device according to claim 1, wherein the first cuff is a femoral cuff and the second cuff is a tibial cuff.

13. An orthotic device having a first and second cuffs connected to one another by an articulating hinge between first and second positions, the orthotic device defining a proximal-distal plane, and an anterior-posterior plane intersecting one another to form an intersection axis, the hinge comprising:
   an upper linkage having first and second pivoting ends;
   a lower linkage having first and second pivoting ends; and
   first and second upright linkages pivotally connected to the first and second pivoting ends of the upper and lower linkages,
   the pivotal connection of the first and second upright linkages forming an instant center of rotation (ICoR) of the hinge located at a superior position relative to the intersection axis, and transmitting either an anteriorly or posteriorly directed force through the second cuff due to a relative displacement of the first cuff relative to the second cuff thereby increasing or decreasing as the hinge articulates said second cuff shifts relative to the first cuff in either a posteriorly or anteriorly direction at least 1 mm from an axis along which the first and second cuffs extend in the second position, relative to when the first and second cuffs extend in a first position.

14. The orthotic device according to claim 12, wherein second cuff shifts relative to the first cuff in either a posteriorly or anteriorly direction at least 1 mm from an axis along which the first and second cuffs extend in the second position, relative to when the first and second cuffs extend in a first position.

15. The orthotic device according to claim 13, wherein the first cuff is a femoral cuff and the second cuff is a tibial cuff.

16. A method for using an orthotic device on a leg, the orthotic device having a lower tibial cuff, an upper femoral cuff, and a hinge comprising upper and lower linkages and first and second upright linkages pivotally connected to the upper and lower linkages, where the pivotal connection forms an instant center of rotation (ICoR) located at an inferior position relative to an anatomical knee joint, the method of using the orthotic device comprising the steps of:
   flexing the anatomical knee joint having the orthotic device;
   shifting the ICoR of the hinge to move to a further inferior position with respect to the anatomical knee joint at greater flexion angles; and
   generating an anteriorly directed force by shifting the lower tibial cuff with respect to the upper femoral cuff.

* * * * *